(12) United States Patent
Riebel et al.

(10) Patent No.: US 9,439,440 B2
(45) Date of Patent: Sep. 13, 2016

(54) BIOFERTILIZERS AND BIOHERBICIDES

(71) Applicant: Scout Materials LLC, Wilmington, DE (US)

(72) Inventors: Michael J. Riebel, Mankato, MN (US); David J. Winsness, Alpharetta, GA (US)

(73) Assignee: GENAREX FD LLC, Alpharetta, GA (US)

( * ) Notice: Subject to any disclaimer, the term of this patent is extended or adjusted under 35 U.S.C. 154(b) by 0 days.

(21) Appl. No.: 13/967,579

(22) Filed: Aug. 15, 2013

(65) Prior Publication Data

US 2014/0051574 A1 Feb. 20, 2014

Related U.S. Application Data

(60) Provisional application No. 61/683,333, filed on Aug. 15, 2012.

(51) Int. Cl.
| | | |
|---|---|---|
| *A01N 65/00* | (2009.01) | |
| *A01N 65/44* | (2009.01) | |
| *A01N 65/40* | (2009.01) | |
| *C05F 5/00* | (2006.01) | |
| *C05C 11/00* | (2006.01) | |
| *C05G 3/02* | (2006.01) | |

(52) U.S. Cl.
CPC .............. *A01N 65/44* (2013.01); *A01N 65/00* (2013.01); *A01N 65/40* (2013.01); *C05C 11/00* (2013.01); *C05F 5/008* (2013.01); *C05G 3/02* (2013.01)

(58) Field of Classification Search
None
See application file for complete search history.

(56) References Cited

U.S. PATENT DOCUMENTS

| | | | |
|---|---|---|---|
| 5,290,757 A | 3/1994 | Christians et al. | |
| 6,509,180 B1 | 1/2003 | Verser et al. | |
| 6,545,191 B1 | 4/2003 | Stauffer | |
| 6,610,867 B2 | 8/2003 | Jakel et al. | |
| 6,703,227 B2 | 3/2004 | Jakel et al. | |
| 7,183,237 B2 | 2/2007 | Blume | |
| 7,937,850 B2 | 5/2011 | Tate et al. | |
| 8,256,134 B2 | 9/2012 | Rehkopf et al. | |
| 8,449,986 B2 | 5/2013 | Riebel et al. | |
| 2005/0229663 A1 | 10/2005 | Blume | |
| 2012/0076915 A1* | 3/2012 | Meier | A23K 1/002 426/624 |
| 2013/0206342 A1 | 8/2013 | Dahmes et al. | |

OTHER PUBLICATIONS

Purdue, "Herbicide Formulations," <http://www.agriculture.purdue.edu/fnr/html/faculty/holt/NRCASupplement.pdf>, published Jan. 7, 2007, p. 1-19.*

Wang, Z., et al., "Use of Constant or Increasing Levels of Distillers Dried Grains with Solubles (DDGS) in Broiler Diets," International Journal of Poultry Science 6(7): 501-507, 2007.*

E. Ximenes et al., "Enzyme Production by Industrially Relevant Fungi Cultured on Coproduct From Corn Dry Grind Ethanol Plants," Applied Biochemistry and Biotechnology, vol. 136-140, 2007: 171-184.*

International Search Report & Written Opinion issued in International Application No. PCT/US2013/055073 dated Feb. 11, 2014; 13 pages.

International Preliminary Report on Patentability, issued in International Application No. PCT/US2013/055073, dated Feb. 17, 2015; 9 pages.

* cited by examiner

*Primary Examiner* — Tracy Vivlemore
*Assistant Examiner* — Monica Shin
(74) *Attorney, Agent, or Firm* — Cantor Colburn LLP

(57) ABSTRACT

Biofertilizer compositions, methods for increasing nitrogen levels in soil and methods of inhibiting undesirable plant growth generally include contacting the soil with a composition comprising dried distillers solubles derived from a dry milling corn ethanol processing; and contacting the soil with the soil in amounts effective to produce the desired result, e.g., increase nitrogen levels, inhibit undesirable plant growth, and the like.

9 Claims, No Drawings

BIOFERTILIZERS AND BIOHERBICIDES

CROSS REFERENCE TO RELATED APPLICATIONS

The present application claims the benefit of U.S. Provisional Application No. 61/683,333 filed on Aug. 15, 2012, incorporated herein by reference in its entirety.

BACKGROUND

Soil nutrients, such as, nitrogen, phosphorus, potassium, and sulfur, as well as trace elements such as iron, zinc, copper, and magnesium, are useful for achieving thriving agriculture and growth of the plants. However, upon repeated planting cycles, the quantity of these nutrients in the soil may be depleted as plants utilize the nutrients. Depletion of nutrient levels in the soil may result in inhibited plant growth and decreased production per acre. To counter this effect, fertilizers have been developed to help replace the depleted vital nutrients in soil so that optimal plant growth and high yields may be obtained.

Fertilizers and herbicides have typically been synthetically produced or isolated using harmful petrochemicals and other chemicals that are now being found to cause cancer, birth deformities, skin reactions and other health issues. Fertilizers and herbicides are commonly used in lawn care, gardening, agricultural, greenhouse and other plan growing environments. With concerns over the health issues related to these products and the growing demand for organic growing and organic products, corn products provide an organic solution for fertilizers and herbicides.

Fertilizers may be classified as either organic fertilizers or inorganic fertilizers. As used herein, the term "organic" generally refers to compounds including a molecular skeleton comprising a carbon backbone. Organic fertilizers are typically made from materials derived from living things. Animal manures, compost, bone meal, feather meal, and nitrogen bearing vegetable protein materials are examples of commonly used commercial organic fertilizers. Inorganic fertilizers, on the other hand, are typically manufactured from non-living materials and include, for example, ammonium nitrate, ammonium sulfate, urea, potassium chloride, potash, ammonium phosphate, anhydrous ammonia, other phosphate salts, and the like.

Chemically active herbicides represent a potential weed control technique. These chemical herbicides may be broken down into pre-emergent and post-emergent herbicides. Pre-emergent herbicides typically interfere with germination of weed seeds, whereas post-emergent herbicides kill the weeds after the weed seeds have germinated and weed growth has begun.

Pre-emergent herbicides may be effective when present at the required dosage at the time weed seed germination is ready to occur. However, this timing issue points out a major problem with respect to pre-emergent herbicides. Specifically, if the pre-emergent herbicide is not applied, or degrades, prior to weed seed germination, the weed seeds are free to germinate and begin growing into mature weeds. Additionally, pre-emergent herbicides are typically weed type specific and are not equally effective against all types of weeds. The timing problem present with pre-emergent herbicides may be avoided by employing post-emergent herbicides and by employing post-emergent herbicides only after the weed seeds have germinated and the weeds are actively growing. However, most available post-emergent herbicides are non-selective herbicides and will therefore kill desirable plants in addition to weeds. Except in the case of genetically modified crops, post-emergent herbicides cannot be used in proximity to crops.

Many pre- and post-emergent herbicides also suffer from another problem. Specifically, many pre-emergent and post-emergent herbicides are either moderately or highly toxic to humans and animals, and may thereby have damaging effects far beyond the intended weed control effect. Toxic herbicides may cause injury either immediately or over the long term to persons applying the herbicides and to persons present when the herbicides are applied. Also, residual concentrations of toxic herbicides that remain in the soil or water after application of the herbicide may pose a significant threat to human beings and to animals, including land-based animals and amphibians and fish, upon contact with the treated area or runoff from the treated area. Furthermore, public alarm about the use of toxic chemicals as herbicides and their potential widespread and long-term effects on environmental quality dictate against the continued use of these toxic herbicides. Uses of chemical herbicides are not permitted in high value organic agriculture.

A drawback of chemically active herbicides coupled with chemical fertilizer, known as weed and feed mixtures, is that they require multiple components. In addition to the serious and harmful side effects of these chemicals, they often require separate applications, have shorter periods of action, and require specially trained personnel to apply, handle, and clean up the material. Another drawback of chemically active herbicides is that they may damage mycorrhiza symbiotic fungal relationship and other beneficial soil life. Chemical fertilizer may be toxic to beneficial soil organisms, for example earthworms, humus, and related organic matter. Destruction of these compounds reduces the ability of the soil to retain nutrients.

Organic vegetable growers do not use chemical herbicides or genetically modified crop varieties in their production. One of the weed control strategies used in the production of high value organic vegetables is the use of corn gluten meal. Testing by organic farmers has shown that corn gluten meal works as a pre-emergent herbicide on a wide variety of broadleaved weeds and some grasses. A pre-emergent herbicide works well for certain types of vegetable production where transplanting is the norm. The herbicidal effects of corn gluten meal seem limited to germinating seed and does not affect most transplanted crops.

Organic fertilizers, on the other hand, are typically not immediately available to plants and require soil microorganisms to break the fertilizer components down into simpler structures prior to use by the plants. This break-down occurs over a time period and may provide for slower release of nutrients.

A relative newcomer to organic farming, corn gluten meal recently emerged as a useful byproduct of the corn milling process for use as an herbicide and fertilizer. Researchers patented the corn gluten meal as a weed control substance in 1991, but it also has other benefits. Most garden centers sell it in large bags in powdered form. While it also forms some or all of pet and cattle food products, corn gluten meal shouldn't be confused with the edible corn meal found in supermarkets.

Corn gluten meal organically inhibits the reproduction of weed seeds in lawns and gardens. The product falls into the family of herbicides known as "pre-emergent" weed killers. Once the weed seeds germinate, and the plants emerge, corn gluten meal has no effect as a weed killer. In fact, its nitrogen content actually acts as a weed fertilizer once the seeds germinate, so timing of the applications for weed control must be carefully controlled. Effective weed prevention with Corn gluten meal is generally recommended using applications of 20 pounds (lbs.) of the product per 1,000 square feet.

Corn gluten meal contains 10 percent nitrogen by weight. Thus, applying 20 lbs. of corn gluten meal for every 1,000 square feet of garden or lawn achieves the commonly recommended 2 lbs. of nitrogen for that area of land. Because that amount corresponds to the recommended rates for organic weed control, it's possible to use one application of corn gluten meal as both a fertilizer and herbicide. The product slowly releases nitrogen into the soil for three to four months.

The primary issue with corn gluten meal used in fertilizers and herbicides is that many of the components within corn gluten meal are not water soluble. For example, corn gluten meal includes water insoluble zein proteins and other insoluble fractions. The issue that corn gluten meal may require many weeks to break down and provide nitrogen and herbicide values greatly limit its effectiveness.

In order for nitrogen to be released, proteins within the corn gluten meal breakdown or undergo a hydrolyzation process, which can take a significant period of time and weather effects to fully break down. In addition, corn gluten meal is a commonly used animal feed and in some cases a human food thus taking away from this food source. In addition gluten meal is limited in the form it is produced, primarily granular forms. Attempts have been made to pelletize this corn gluten meal which also requires some type of "binder" such as sugars or other forms of binders. This further inhibits the release rates and breakdown of the corn gluten material.

The wet milling of corn produces corn gluten meal as one of its primary products. Corn gluten meal is one of many products extracted from corn during the wet milling process. A description of processes that produce corn meal is seen in U.S. Pat. No. 6,610,867 to Jakel et al. which is hereby incorporated by reference in its entirety. Other descriptions are seen in U.S. Pat. No. 6,703,227 to Jakel et al, U.S. Pat. No. 6,545,191 to Stauffer, and U.S. Pat. No. 6,509,180 to Verser which are hereby incorporated in their entireties by reference. Corn gluten meal is extracted from corn following an acid bath soaking period. Corn gluten meal may be spread on the surface of the soil after seeding or tilled in shallowly prior to seeding. The weed suppression effect of corn gluten meal continues for weeks after application. The use of corn gluten meal in this fashion is permitted for use in organic agriculture. The National Organic Standards Board (NOSB) lists corn gluten meal as a organic approved herbicide in the restricted class. However, the corn from which the corn gluten meal is derived cannot be a genetically engineered variety.

Another drawback with the use of corn gluten meal as an herbicide has been its relatively high cost. Corn gluten meal has been in high demand, especially in Europe, as both chicken and cattle feed. Corn gluten meal may produce brightly colored yokes when fed to laying hens and this is a consumer preference.

The prior art also teaches of chemical modifications to corn gluten meal using various acid treatments to create a corn hydrolysate which has been shown to have improvements for bioherbicide applications. This requires significant additional processing, cost and processing with potentially harmful chemicals. Corn gluten meal in its raw form is currently an expensive ingredient commonly used in animal food and further chemical process further adds to its cost.

U.S. Pat. No. 5,290,757 found that hydrolyzed proteins from corn gluten meal provide improvements over standard corn gluten meal. This requires further processing of the corn gluten meal by means of a secondary process adding various enzymes and corn hydrosylate.

Alternatives to corn gluten meal have been evaluated. For example, U.S. Pat. No. 7,183,237 to Blume teaches a method for the usage of distillers grain as a herbicide and fertilizer. This method uses standard dried distillers grains (DDG) which is the water insoluble fraction of the well known corn-to-ethanol production process. Although less expensive than corn gluten meal, DDG has less nitrogen bearing proteins and high percentages of water insoluble corn fiber which is not as effective as corn gluten meal.

Thus there is a need for a low cost water soluble form of organic corn protein with high nitrogen bearing content and a very high degree of water solubility that can be produced in a wider range of formats from pellets, sheets, granular and other forms. In addition, there needs to be a material with self binding nature wherein other additives can be added to modify the nature of an organic fertilizer and herbicide materials and related process. In addition there needs to be a solution that is both effective and lower cost than corn gluten meal as to better promote the usage of organic and chemical free fertilizer/herbicides.

BRIEF SUMMARY

Disclosed herein are biofertilizers, bioherbicides and methods of use.

In one embodiment, a method for inhibiting growth of undesirable plants in soil comprising contacting the soil with an amount of a dried distillers solubles derived from corn ethanol processing in an amount effective to inhibit growth of the undesirable plants.

In another embodiment, a method for increasing nitrogen levels in soil, the method comprises contacting the soil with a composition comprising dried distillers solubles derived from a dry milling corn ethanol processing in an amount effective to increase nitrogen levels in the soil to a desired amount.

A biofertilizer composition comprises dried distillers solubles having a moisture content less than 25 percent by weight and an oil content of 3 to 15 percent by weight, wherein the dried distillers solubles is derived from a dry milling corn ethanol process.

The disclosure may be understood more readily by reference to the following detailed description of the various features of the disclosure and the examples included therein.

DETAILED DESCRIPTION

Various non-limiting embodiments of the present disclosure present an organic fertilizer/herbicide comprising dried distillers solubles. The methods of increasing the nitrogen content of soil, methods of promoting plant production and/or inhibiting growth of undesirable plants and methods of fertilizing/herbicide application to plants are also described.

As used herein, the term dried distiller's solubles (DDS) generally refers to a byproduct of the corn-to-ethanol fermentation dry milling process, and more particularly, to the soluble portion of whole stillage in dried form. In the dry milling process, corn is first screened and ground to a flour. The resulting flour is combined with water and the starch within the corn is conventionally hydrolyzed into sugar by liquefaction and saccharification. The mixture is then fermented with yeast to convert the sugar into ethanol and carbon dioxide. About 30% of the mass of each kernel of corn accepted by corn ethanol producers is converted into ethanol in this manner. The output of fermentation, a mixture of ethanol, water, protein, carbohydrates, fat, minerals, solids and other unfermented components, is then distilled to boil off ethanol for recovery, purification and sale, leaving the remainder of the mixture in the bottom of the distillation stage.

The remainder of the mixture at the bottom of the distillation stage is referred to as whole stillage (WS) and is typically subjected to a press or centrifugation process to separate the coarse solids from the liquid. The liquid fraction is commonly referred to as distillers solubles or thin stillage (TS). TS is frequently concentrated in an evaporator to become condensed distillers solubles (CDS), which is also commonly referred to as syrup or thin stillage concentrate. By the time CDS exits the evaporators, its protein and other constituents may have changed significantly due to continuous treatment during the fermentation process with hot water, enzymes, caustic, acid, urea and/or other chemicals, at times under pressure and/or vacuum, for more than two days. Many of these process conditions are severe and are generally known to facilitate at least some degree of hydrolysis, denaturation and other presently favorable reactions and reactants.

The TS and its more concentrated form of CDS form are generally comprised of water, protein, fat, carbohydrates, ash, and relatively minor amounts of other fermentation byproducts. At least some of the protein is water-soluble. The fat is substantially comprised of glycerides and is present in a free, bound and/or emulsified state. The carbohydrate fraction is further comprised of various sugars, partially-hydrolyzed starch, and insoluble polysaccharides (cellulose, hemicellulose and lignin). Ash includes residual minerals. Fermentation byproducts include glycerol, lactic acid, acetic acid, yeast, and the like.

Drying the liquid fraction, e.g., TS and/or CDS, produces the dried distillers solubles (DDS), which as described herein can be used as an herbicide and/or fertilizer.

Exemplary drying methods include processes using standard drying equipment, including, without limitation, evaporation, spray drying, vented extrusion, belt drying, and pulse combustion drying. Some methods and apparatus are described in U.S. patent application Ser. Nos. 12/215,214 and 12/398,984, which are incorporated herein by reference in their entireties. Drying CDS would generally preserve the solubles and suspended material in TS or CDS and may allow for storage and/or distribution. The DDS obtained from the TS or CDS can be in the form of particles, powder, pellets, agglomerates, and other forms.

In some instances, the TS or CDS are subjected to a high temperature drying process to form DDS, which reportedly has been used as a thermoplastic additive with a metal oxide and fiber in the preparation of extruded articles. For example, U.S. Pat. No. 8,449,986 to Riebel et al. describes various biocomposite compositions that include dried distillers solubles, metal oxide, and fiber.

In other embodiments, the DDS are subjected to a multistep low temperature drying process to form particles and granules such as is disclosed in U.S. patent application Ser. No. 13/768,747, incorporated herein by reference in its entirety. The multistep low temperature drying process generally includes a fluidized bed apparatus configured to heat CDS (or thin stillage) to a temperature less than 300° F. in most embodiments, less than 250° F. in other embodiments, and less than 200° F. in still other embodiments. In one embodiment, the process generally includes spraying or conducting CDS through one or more nozzles and subjecting the resultant output to a flow of heated gases within a chamber to evaporate at least a portion of the moisture from the CDS and form discrete particles and granules. The discrete particles and granules are then carried from the chamber by means of a fluidized bed to facilitate additional drying and/or cooling that may include additional moisture removal. The fluidized bed includes a perforated surface in fluid communication with a fluidizing medium. The bed may include a single or plurality of zones, where the first zone introduces a heated inert fluidizing medium and additional zones facilitates cooling of the particles and/or granules prior to discharge from the apparatus. An exemplary apparatus is provided in the FIGURE. The perforated surface of the fluidized bed can be a fixed bed, perforated moving conveyor, a perforated vibrating bed, a vibrating perforated moving conveyor or other.

The drying process is configured to provide the DDS in a powder and/or granular form with a moisture content of less than about 25 percent by weight in most embodiments, a moisture content of about 3 to about 20 percent by weight in other embodiments, and a moisture content of about 5 to about 12 percent by weight in still other embodiments. The resulting DDS is a relatively tacky material, is relatively high in water soluble proteins, and retains a small percentage of residual oils. As used herein, weight percent (wt-%) percent by weight, % by weight and the like are synonyms that refer to the concentration of a substance as the weight of that substance divided by the weight of the composition and multiplied by 100. Unless otherwise specified, the quantity of an ingredient refers to the quantity of active ingredient.

In some embodiments, the DDS or TS or CDS may be pretreated by chemical modification of proteins or amino acids in the material. For example, CDS typically has a pH of about 4. Modifications can include, for example, treating proteins in CDS with an acid, base or other agent that alters the structure of one or more of the amino acid side chains, which, in turn, alters the character of the protein and/or amino acids. For example, the high glutamine and asparagine of prolamines, particularly zein from corn, provides a means for manipulating the charge characteristics of the protein by deamidation, thereby providing a wide range of hydrophobicity. In one embodiment, deamidation involves mild acid catalyzed deamidation at a pH of about 1 at temperatures from about 25° C. to about 65° C. for a period of time sufficient to accomplish the desired level of deamidation. In some embodiments, acids that form stable dispersions and are useful within these classes include, without limitation, lactic acid, citric acid, malonic acid, phosphoric acid, fumaric acid, maleic acid, maleic anhydride, maleated propylenes, glutaric acid, transaconitic acid, acetic acid, propionic acid, sorbic acid, cysteine and glycyl glycine. In one embodiment, lactic acid in the form of polylactic acid is used. In another embodiment, maleated propylenes, such as G-3003 and G-3015 manufactured by Eastman chemicals are used.

Other examples of chemical modification include, without limitation, esterification of the proteins contained therein with fatty alcohols and acylation of the proteins with fatty anhydrides.

In some embodiments, it may be desirable in some applications to remove at least a portion of the oil or other constituents contained in TS or CDS prior to drying to form the DDS with the desired moisture content of less than 25 percent The amount of oil and/or other constituents removed can be used to tailor the properties. In most embodiments, the oil content in the DDS product material is from 3 to 15% by weight although higher or lower amounts of oil may be desired in certain applications.

Although not required, removal of the oil can advantageously increase concentration of other constituents within the DDS that are beneficial for fertilization applications. For example, in addition to the water soluble proteins and oil/fatty acids, the TS and CDS can contain soluble potassium and phosphorous in addition to some other trace minerals and compounded. The removal of the fatty acids/ corn oil from the CDS is preferred in some embodiments because the oil may function to inhibit the break down of the proteins into nitrogen. Moreover, removal of oil creates a faster release of key materials into the soil. The removal of oil also assists in concentrating other key soil fertilizer components such as potassium and phosphorous. Table 1 provides a comparison of CDS with and without at least a portion of the oil removed, thereby demonstrating the effect on various components as a function of oil removal.

TABLE 1

| TEST ANALYSIS | CDS | DEOILED CDS |
|---|---|---|
| Phosphorous | 1.81% | 2.91% |
| Potassium | 2.65% | 3.92% |
| Magnesium | 0.8% | 1.3% |
| Sulfur | 1.57% | 1.54% |
| Copper | 8.3 ppm | 4 ppm |
| Iron | 135 ppm | 170 ppm |

(Source: *GS/Midwest Laboratory Report & Dakota Gold* Published specifications)

As shown above, the deoiling process applied to this particular CDS provided over a 60% increase in the key phosphorous/potassium levels that are important fertilizer ingredients. In addition, increases in magnesium and iron were observed, which also desired materials to have for soil improvements. The copper levels dropped, which is also desirable. Removal of additional oil can be expected to provide even greater increases and decreases where indicated. It can be expected that the deoiling process applied to any CDS will produce similar results.

Prior to the drying step, various additives can be added to the CDS that not only assist in the drying efficiencies, but also provide added benefit for fertilizers, herbicides and insecticide applications. Additives can be blended with liquid CDS prior to evaporation processing or directly after deoiling processes before final drying. By "wet compounding" or mixing, this improves the dispersion of various additives. Material additives can include, but are not limited to, other organic fertilizers; urea; worm casings; bone meal; natural proteins; additional phosphorous materials; additional potassium materials; additional ingredients used in fertilizers, herbicides or insecticides; binders for controlled release rates; additional minerals; pH modifiers; oxide minerals; cellulose and paper mill sludge; fish fertilizer; binders; preservatives; insecticides; animal repellents; other forms of additives commonly used in fertilizer/herbicide products; and the like.

With regard to the herbicide function, DDS may be used alone or in other embodiments, with an active aerobic compost, earthworm castings, or other appropriate organic materials. When applied to the soil, DDS blended with other organic materials greatly increases the diversity and biomass of a wide variety of fungi and bacteria, as well as micro-crustaceans and other micro-fauna. Many of the fungi and bacteria are specialists at decomposition of cellulose, or generalists that can also decompose some cellulose. The fungi and bacteria undergo a population increase when the DDS or the combination of DDS and active compost are applied to the soil. A massive inoculation of the fungi and bacteria occurs as a function of time that dominates the soil. Corn has a large store of energy in its seed; the rate of growth of its root outstrips any biological damage. Because the DDS is ground, condensed, seed and nitrogen bearing proteins, the soil organisms that specialize in eating these materials are the ones which reproduce at explosive rates. Although most seeds resist the decomposing effects of these organisms by various methods in the seed coat, the DDS is exposed and provides uninhibited feeding to the soil organisms. In areas where the soil organic matter content is below 2% the amount of soil micro-flora is reduced. In these types of areas, the mixing of fresh aerobic compost made of most any organic matter, such as vermi compost, will provide an abundance of the useful micro-flora to inoculate the DDS and begin the rapid reproduction of soil organisms. In areas which are using this method for successive years, the addition of compost may be unnecessary after the first year.

Once the microorganisms begin their rapid reproduction cycle, most germinating seed is attacked. Depending on the species of the germinating seed, the germinating seed is either killed or begins a battle to try to grow faster than the soil organisms can devour the growing root tips. Even if the weed survives this battle, the germinating seed will have had its strength sapped and its growth is stunted. Such stunting of the growth of the weeds is often all that is necessary in crop production, as the stunted plants then become shaded by the closed canopy of the faster growing crop plants. The closure of the canopy over the weeds reduces or eliminates sunlight, and the weeds wither, die, stop growing, or have their growth slowed to a level which is not a threat to the crop plants.

Although wet mixing or compounding may be preferred in some embodiments given that wet mixing provides a more uniform dispersion or may assist in the efficiency of drying, these additives can also be blended with the final dried DDS powder prior to granulation, pelleting or sheeting processes by means of simple mechanical mixing.

The DDS has a unique nature in the fact that it has a natural adhesive nature for binding. Given this unique nature as compared to other bioherbicides and biofertilizers such as corn gluten meal or dried distillers grains that do not have this level of functionality, DDS can be formed, pelleted or sheeted in a wider range of products for these specific applications. In addition, dry or liquid additives can be blended prior to pelleting to enhance the organic fertilizer or herbicide functions.

By way of example, the DDS can be placed in a rotary drum or other forms of granulating equipment to create a fine "ball" of a specific size. Optionally, dry powder additives can be added to coat the outside of the granular particles. DDS can be direct extruded into a elastomeric film without the addition of any additives or plastics. This allows the development of agricultural films that are highly biodegradable, but also during biodegradation provides a fertilizer and herbicide effect, thus providing multiple functionality for the growing of various row crops such as vegetables and a wide range of other agricultural crops. In an agricultural film form, the final DDS film can be coated or secondary processed to meet specific product and applications requirements. Coatings can also be biodegradable, but maybe designed to control the rate of biodegradation. Coatings or secondary top layer films can comprise of, but not limited to: biodegradable plastics, natural waxes, natural latexes, plastic films, UV cured coatings, starch based coatings, protein based coatings, and other natural or synthetic coatings or films.

In other embodiments, the DDS can also be re-dissolved to water in specific amounts along with various additives, preservatives, fertilizer, herbicides or insecticides for liquid applications.

According to other embodiments, the organic DDS fertilizer may comprise an organic acid fermentation and residual amount of sulfur and other trace minerals and are positive for soil conditioning and soil health. Materials such as sulfur and other minerals are helpful in building healthy soil. Trace minerals are contained within the DDS material including, but not limited to, magnesium, sulfur, copper, iron, manganese and zinc.

Most fertilizers provide three primary measurements of their effectiveness based on three values: nitrogen, phosphorous, and potassium, which is also commonly referred to as the NPK rating and is an important part of deciding whether or not fertilizers are appropriate or even necessary for your garden and landscaping. By applying DDS, the various nitrogen fixing bacteria present in the soil are greatly multiplied in numbers and will carry out nitrogen fixation from the air and the soil. All natural nitrogen is replenished in the soil after each harvest when plant matter and decaying plant matter is turned into humus thereby creating a simultaneous all natural regeneration cycle in the soil. Nitrogen and nitrogen from soluble proteins within the DDS provides a good source of nitrogen release.

Phosphate is taken up by plants from soils, utilized by animals that consume plants, and returned to soils as all natural residues decay in soils. Much of the phosphate used by living organisms becomes incorporated into all natural compounds. When plant materials are returned to the soil, this all natural phosphate will slowly be released as in all natural phosphate or be incorporated into more stable all natural materials and become part of the soil all natural matter. The release of natural phosphate from all natural phosphates is called mineralization and is caused by microorganisms breaking down all natural compounds.

DDS naturally contains phosphorous, a growth enhancer that greatly promote the growth of (Phosphate Solubilizing Bacteria) which fixes the renewable all natural Phosphate into a natural form which is taken up by the plant. Therefore, the phosphate is constantly renewed in the soil as the all natural residues decay in the soil. The use of chemical fertilizers on the other hand destroys these beneficial PSB and thus the available phosphate is not used by plants because they are still in their all natural forms.

Sources of potassium include dead plant material, manure, compost, granite dust, greensand, and seaweed.

DDS aids in the conversion of the potassium found in dead plant material especially after each harvest where the dead plant material is rotavated together with the soil. Therefore, the potassium is constantly renewed in the soil as the all natural dead plant matter decays in the soil and is converted to in all natural form by the bacteria present in the soil which has been greatly increased in numbers by DDS, which multiplies in the soil and fixes the potassium to in all natural form to be taken up by the plants.

The following examples are presented for illustrative purposes only, and are not intended to limit the scope of the invention.

Example 1

In this example, condensed distillers solubles from a dry mill ethanol plant in a high water content water emulsion was placed into an evaporator to bring down the moisture content. Corn oil was removed through a centrifugal process. The remaining thicker liquid was dried using a combination of spray drying and fluidized bed drying to provide as total moisture content of less than 15%. The drying temperature was less than 200° F. as to preserve the proteins and retain a bright yellow appearance of the final powder material.

Example 2

In this example, the powder of example 1 was mixed with water at a ratio of 50% water to 50% PCDS by weight. With minimal mixing, the powder went into full solution. The glass container was left sitting for over 2 hours and the powder did not come out of solution. For comparison, DDG and Corn Gluten Meal were also mixed with water at the same ratio. Within minutes, a layer of solids were seen at the bottom of the glass container for each mixture.

Example 3

In this example, the PCDS (dried oil removed CDS) material of example 1 was analyzed. This was then compared to the analysis of a non deoiled CDS. From this analysis, improvements of potassium and phosphorous levels and reduction of copper were observed.

Example 4

In this example, the PCDS material was processed into various size particles ranging from less than 0.004 inches to over 0.5 inches in average diameter. The material was then broadcasted over a specific lawn area prior to a rain of 0.3 inches. After the rain, the particles having an average diameter of less than 0.1 inch were not visible whereas larger particles were reduced in size by approximately 50%.

Example 5

In this example, the PCDS material was placed in a twin screw extruder and extruded at temperatures at 170° F. Using a round rod die of 0.2 inches in diameter, the material flowed similar to a molten plastic material and was cut into pellets. Next, the pellets were placed into a flat compression molding machine and pressed into a sheet of less than 0.050 inches. The resultant material was similar in feel to that of an elastomer or rubber sheet. The sheet was then immersed in a container of water. Within about a minute, the surface of the sheet softened and a powdery-like substance could easily be scraped off of the surface. Within about 4 hours, the sheet was sufficiently soft and degraded wherein with simple stirring completely dissolved the sheet.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for inhibiting growth of undesirable plants in soil comprising:

contacting the soil with a composition consisting of dried distillers solubles derived from a dry milling corn ethanol processing in an amount effective to inhibit growth of the undesirable plants.

2. The method of claim 1, wherein the composition is in sheet form.

3. The method of claim 1, wherein the composition has a moisture content of less than 25 percent by weight.

4. The method of claim 1, wherein the composition is in granular, powder or pellet form.

5. The method of claim 1, wherein the composition is a solution.

6. The method of claim 1, wherein the dried distillers solubles is formed from a substantially liquid fraction of a whole stillage byproduct and is dried to a moisture content of less than 25 percent by weight at a temperature less than 300° F.

7. The method of claim 1, wherein the dried distillers solubles is chemically modified prior to applying the composition to the soil.

8. The method of claim 1, wherein the dried distillers solubles has an oil content of 3 to 15 percent by weight.

9. The method of claim 1, wherein contacting the soil with the composition consisting of the dried distillers solubles is prior to emergence of the undesirable plants.

* * * * *